United States Patent [19]

Abler

[11] Patent Number: 5,450,750

[45] Date of Patent: Sep. 19, 1995

[54] BODY VOLUME MEASUREMENT CHAMBER

[75] Inventor: Joseph H. Abler, Brookfield, Wis.

[73] Assignee: Abler Data System, New Berlin, Wis.

[21] Appl. No.: 269,500

[22] Filed: Jul. 1, 1994

[51] Int. Cl.⁶ .......................................... G01F 17/00
[52] U.S. Cl. .................................................. 73/149
[58] Field of Search ................................. 73/149, 433

[56] References Cited

U.S. PATENT DOCUMENTS

| | | | |
|---|---|---|---|
| 4,270,381 | 6/1981 | Demaray | 73/149 |
| 5,105,825 | 4/1992 | Dempster | 73/149 |
| 5,231,873 | 8/1993 | Lindberg | 73/149 |

*Primary Examiner*—Robert Raevig
*Attorney, Agent, or Firm*—Quarles & Brady

[57] ABSTRACT

A chamber for determining the volume of a patient for tissue density calculations provides controlled and continuous volume changes in the chamber by means of increasing offset between connected tanks of water, one of which communicates to the chamber to withdraw air from the chamber as its water level falls. Continuous pressure and volume data is thereby obtained allowing rapid determination of the patient volume through an application of Boyle's law. The chamber includes a self-sealing design in which the reduced air pressure of the chamber holds its lid in place. The pressure difference is maintained by a patient's holding down of a handle closing a pressure release valve permitting rapid egress by the patient when the handle is raised.

8 Claims, 2 Drawing Sheets

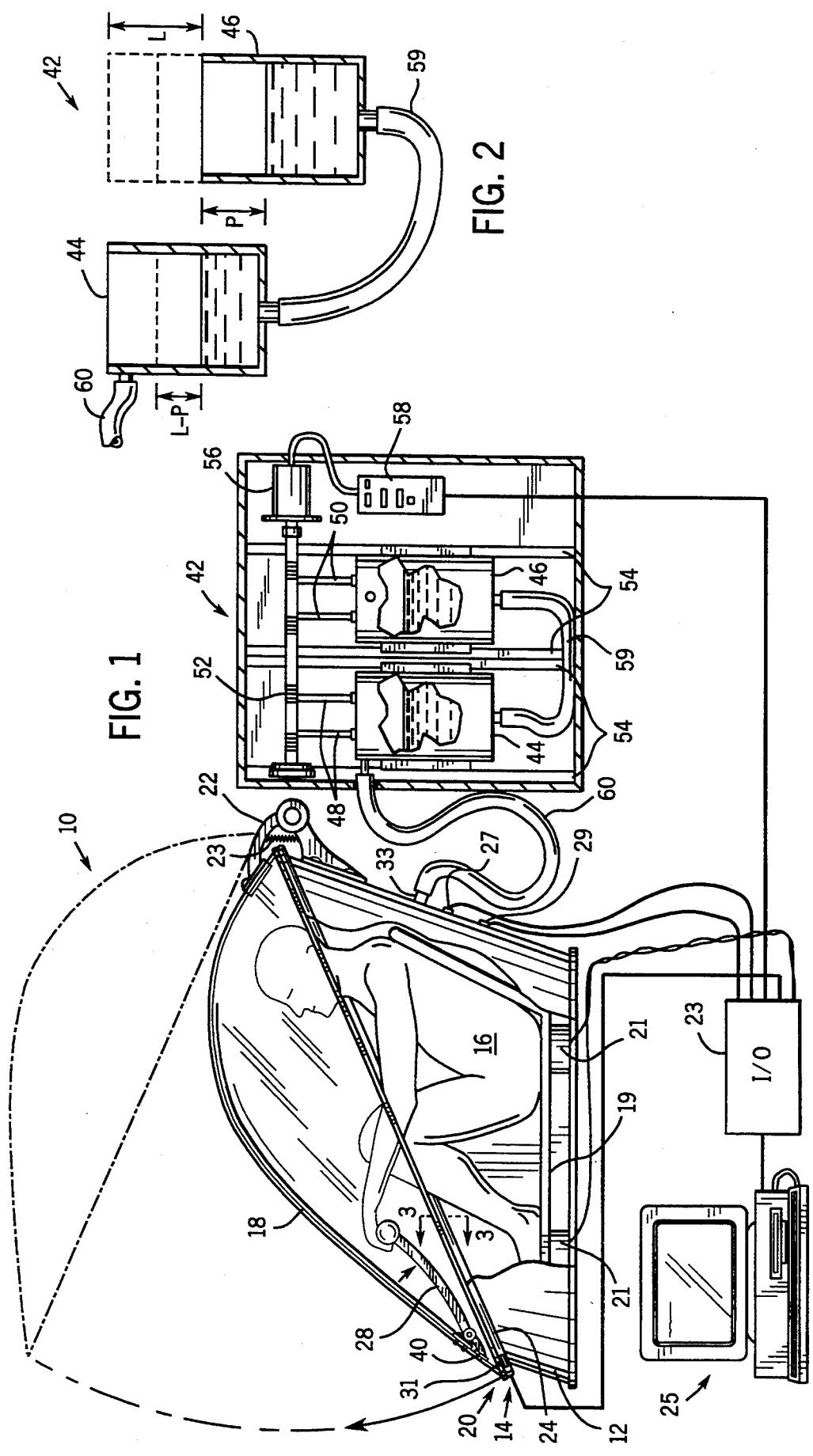

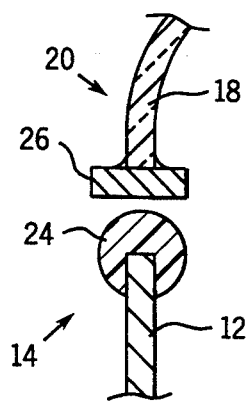
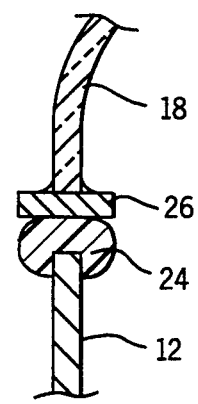
FIG. 3a　　　　　FIG. 3b
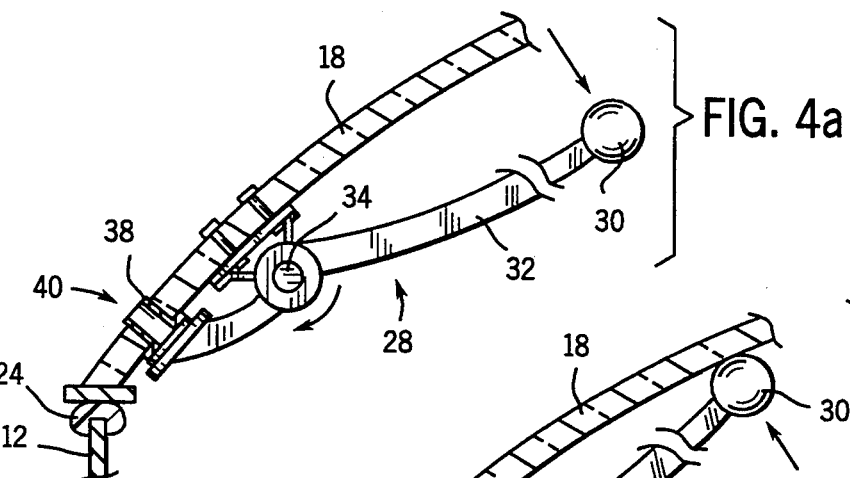
FIG. 4a
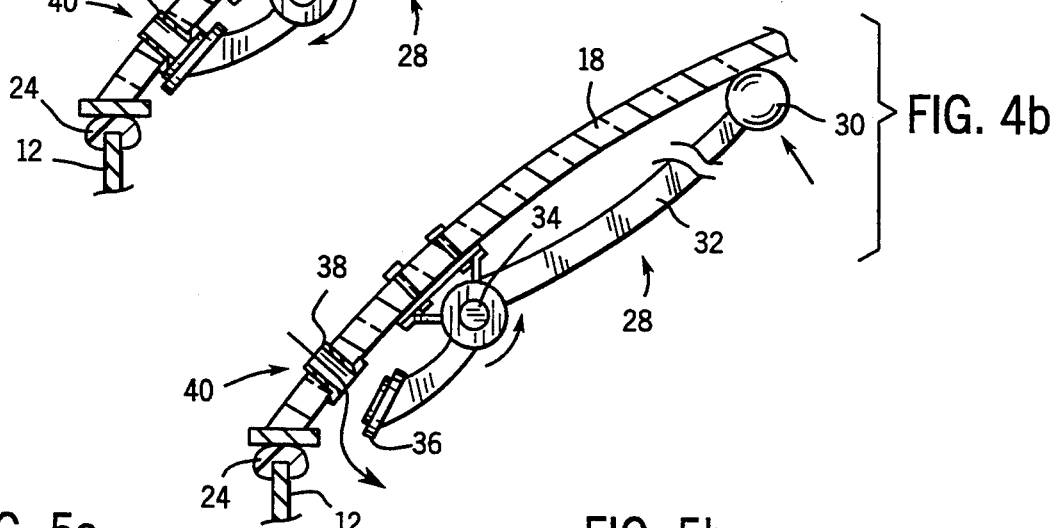
FIG. 4b
FIG. 5a
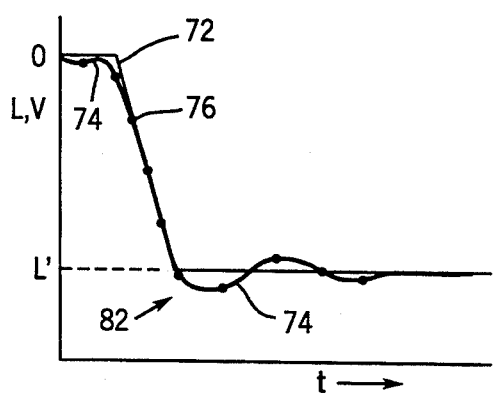
FIG. 5b
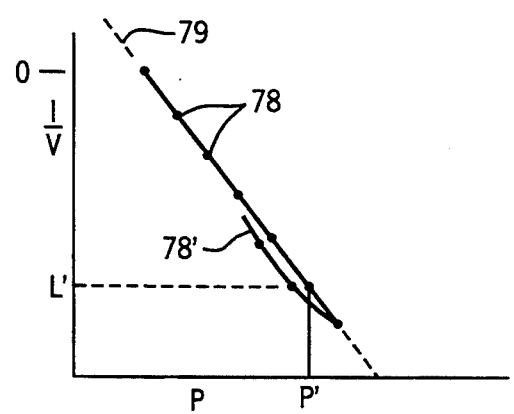

BODY VOLUME MEASUREMENT CHAMBER

FIELD OF THE INVENTION

The invention relates generally to equipment for measuring the volume of an individual or animal as part of the calculation of body density, and in particular equipment for determining percentage of body fat of humans or animals.

BACKGROUND ART

There is considerable interest in the rapid assessment of average body density, particularly for athletes, insofar as average body density provides an indication of total body fat. For example, percent body fat may be estimated according to the volume formula:

$$\% \text{ fat} = (4.57/\text{density} - 4.14) * 100.$$

Such density measurements are currently made by the so-called hydrostatic method in which the individual is submerged in water and the volume of water displaced by the individual's body is determined providing an indication of the individual's total body volume. Total submersion of an individual, as is required by this method, is inconvenient and stressful to the individual.

Another drawback to the hydrostatic method is the fact that the volume so measured includes the air-filled lungs and respiratory track. Including these air-filled volumes erroneously lowers the apparent density of the individual's tissues. Whereas fat is approximately nine-tenths as dense as nonfat tissue, air is approximately 1000 times less dense than nonfat tissue. Thus, even small amounts of measured air can provide serious error in the calculation of density when used to compute percentage of body fat.

Accordingly, interest has developed in less severe methods of measuring body volume. One method encloses the individual in an airtight chamber connected to a second pressurized chamber of known volume. Pressure measurements are made in the chamber housing the individual both before and after a valve is opened connecting that chamber to the second pressurized chamber. Knowing two pressures and the incremental volume of the second chamber permits one to calculate the volume of the individual contained in the first chamber. This calculation employs Boyle's law which states that for a given amount of gas at a constant temperature, the pressure of the gas times its volume will be constant.

The second chamber in this method provides an accurate way of increasing the total volume of the system, but is cumbersome and slow. The second chamber must be pre-pressurized and measurements are only made after the first and second chamber have reached a pressure equilibrium. For use with a human, and for significant pressure changes, this speed of equalization must be moderated to prevent discomfort to the individual, particularly with respect to pressure across the individual's eardrum.

These problems of low measurement speed are avoided by methods that subject the patient to subsonic pressure fluctuations. By using a dynamic measurement process, small leaks in the chamber may be tolerated and thus the need for a separate pre-pressurized volume can be avoided. Nevertheless, these dynamic techniques are generally restricted to small amplitude pressure variations and thus have less potential for high accuracy measurement. Further, the devices are complex in construction.

SUMMARY OF THE INVENTION

The present invention provides a chamber for measuring the volume of a breathing patient at a pressure level substantially lower than that obtainable with dynamic techniques using subsonic waves while avoiding the need for a pre-pressurized second volume. Importantly, the invention permits the taking of a series of pressure and volume measurements as the pressure in the chamber is reduced to a predetermined value. These multiple measurements provide improved accuracy and faster operation.

A hydraulic piston formed from two interconnected fluid filled cylinders is used to change the pressure of the chamber thereby providing a simple and leak-less pump suitable for automatic operation. A falling liquid level in one of the cylinders communicating with the chamber holding the subject, increases the effective volume of the chamber in a way that may permit instantaneous volume measurements. The volume increase at any given instant is equal to the relative height offset between the cylinders minus the pressure differential between the cylinders expressed as a height of a column of the contained liquid.

The chamber is operated under negative pressure to provide a self-closing door seal preventing the infusion outside air. A handle grasped by the subject and used to close the chamber also closes a pressure relief valve. When the handle is released, the pressure relief valve opens restoring pressure to the chamber so that it may be easily opened.

Specifically then, the apparatus includes a substantially air tight chamber having a chamber volume sized to receive a subject. A pump communicating with the volume changes the air pressure within the chamber during a test period and a pressure gauge communicating with the chamber produces a pressure signal indicating the pressure within the chamber volume. The pressure signal is sampled at a plurality of times during the test period by a sampling circuit to produce sample pressure values which may be combined to predict a static pressure. This predicted pressure is used to calculate the volume of the patient which may be displayed on a display device.

It is thus one object of the invention to provide a volume determining chamber having the accuracy obtainable with static methods and yet which allows the measurement and combination of dynamic pressure and volume data to more quickly and accurately reach a determination of the volume of the subject. The sampling time may include a period longer than a typical respiration period so as to eliminate respiratory artifacts. The combination may involve a linear regression of the pressure values to associated volume values to anticipate or predict the ultimate static pressure.

The pump may be constructed of two containers, the first container having a first and second opening and the second opening communicating with the chamber volume. The second container may have a first opening communicating with the first opening of the first container. The second container is mounted so as to move vertically with respect to the first container. A liquid placed in the first and second containers may flow therebetween with changes in the relative vertical offset of the two containers thereby moving air between the chamber volume and the first container when liquid flows between the first container and the second container in response to that vertical offset. Instantaneous volume may be calculated from the displacement of the two containers and the pressure signal in the chamber.

Thus, it is another object of the invention to provide a simple and effective volumetric pump for changing the volume of the chamber rapidly to a predetermined pressure value while providing a steady stream of volume and pressure data that may be used to anticipate and measure the static pressure condition ultimately to be achieved.

The chamber may include an aperture with a first lip through which the subject may be received into the chamber volume. A lid has a second lip that may abut the first lip when the lid is in a closed position over the aperture. In the closed configuration, the pump may be arranged to decrease the air pressure within the volume so as to draw the lid and chamber together to form an air-tight enclosure. The lips may include one or more elastomeric seals and the lid may be otherwise biased to an open position by a spring. A handle attached to the lid may permit the subject to close the lid against the spring bias and to simultaneously close a pressure relief valve permitting the negative pressure within the chamber to further close the chamber. Release of the handle releases the pressure relief valve permitting the spring biasing of the lid to open the lid against the reduced pressure differential.

Thus it is another object of the invention to provide a simple design for a volume measuring chamber that permits simple ingress and egress by the subject.

In use, the subject may be enclosed in the substantially airtight chamber and the pressure of air reduced during a test period after which the change in pressure is determined. This determined pressure may be compared to a standard pressure representing the result of a similar reduction in pressure without the presence of the subject. Both the measured and standard pressure may be compared to calculate the volume of the patient.

Thus, it is another object of the invention to provide a measurement protocol which eliminates the effects of small changes in the chamber volume caused by the compressive action of outside air pressure and possible small sources of outgassing. The use of a standard pressure permits compensation for these effects.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

BRIEF DESCRIPTION OF THE DRAWINGS

FIG. 1 is a side elevational view of the apparatus of the present invention showing the chamber for holding an individual to be measured and showing a pump for reducing the air pressure in the chamber under the control of a computer;

FIG. 2 is a schematic view of the pump of FIG. 1 showing the calculation of instantaneous pump displacement volume as a function of pressure and pump offset;

FIGS. 3(a) and 3(b) are cross-sections of the seal between the lid and base of the chamber of FIG. 1 in the opened and closed position, respectively, showing compression of the intervening gasket as pressure in the chamber is reduced;

FIGS. 4(a) and 4(b) are cross-sectional views through the lid of the chamber of FIG. 1 showing the handle used to close the lid of the chamber and simultaneously close a pressure release valve which may be opened to provide rapid egress from the chamber;

FIG. 5(a) is a plot of pump displacement and pump offset as a function of time showing multiple data readings as the pressure is reduced; and FIG. 5(b) is a plot of volume versus pressure sharing the same ordinate as the graph of FIG. 5(a) and illustrating the ability of the present invention to provide multiple data points that may be used to estimate and further refine a static pressure reading.

DETAILED DESCRIPTION OF THE PREFERRED EMBODIMENT

Referring to FIG. 1, a volume measuring chamber 10 includes a tub-shaped base 12 having an upper annular lip 14 through which an individual 16 may enter. After entry, the individual 16 may be seated on a platform 19 attached to the bottom of the base 12.

The platform 19 is attached to the bottom of the base 12 by means of two load cells 21 which provide electrical signals permitting the weight of the individual 16 to be measured. These electrical signals are provided to a microprocessor input/output (I/O) card 23 attached to a computer 25. The microprocessor I/O card includes a microprocessor and associated memory, together with an analog input multiplexer, an analog to digital converter, digital input and output lines, a display and a serial communications ports, all of which are well known in the art, to collect and pre-process data and to provide an interface to programs running on the computer 25 that makes use of the weight information from the load cells and other data as will be described in the computation of the density of the individual 16. A temperature transducer 27 and a pressure transducer 29 are also attached to the base 12 for making temperature and pressure readings of the air within the chamber 10 and providing those readings via cables to the microprocessor I/O card 23 for use by the program running on the computer 25. A fan (not shown) contained within the chamber 10 insures that the temperature measured by the temperature transducer 27 represents the average temperature of the air within the chamber 10. Finally, the rearmost surface of the base 12 is breached by an orifice 33 providing a means for removing and adding air to the chamber 10 as will be described.

A dome-shaped Plexiglass lid 18 may be closed over the base 12 so that a lower lip 20 of the lid 18 abuts the upper lip 14 of the base 12. The lid 18 is generally hinged to the base 12 by means of a hinge 22 attached between the rearmost upper edge of the base 12 and the rearmost lower edge of the lid 18. Alternatively, the lid 18 may be hinged on the side. The hinge 22 includes a biasing spring (not shown) sufficient to counterbalance the weight of the lid 18 so that the lid 18 may be easily moved between the open and closed position absent the effect of other forces as will be described. In the open position, the lid 18 rises off of the base 12 to permit the individual 16 to exit from the base 12. When the lid 18 is closed on the base 12, the individual 16 is contained in a closed volume of the chamber 10.

A proximity switch 31 is positioned on the front upper lip 14 of the base 12 to provide an electric signal indicating the closure of the lid 18 on the base 12. Again, this electrical signal from the proximity switch 31 is provided to the microprocessor I/O card 23 to the computer 25.

Referring now to FIGS. 1, 3(*a*) and 3(*b*), an elastomeric gasket 24 encircles the upper lip 14 of the base 12 to abut a planar horizontal flange 26 attached along the lower lip 20 of the lid 18. When the lid 18 is closed upon the base 12 as shown in FIG. 3(*b*), the flange 26 presses against the elastomeric gasket 24 compressing and deforming the same to produce an air tight seal between the lid 18 and the base 12 at upper and lower lips 20 and 14. This compression may produce a small change in the total volume of the chamber 10 as will be described further below.

Referring now to FIGS. 1, 4(*a*) and 4(*b*), the lid 18 may be moved from the open position to the closed position by means of a handle 28 accessible at the inner surface of the lid 18 to be grasped by the individual 16 when seated on the platform 19. The handle 28 includes a grip 30 that may be held by one or both hands of the individual 16. The grip 30 is attached by means of a lever arm 32 to a pivot 34 affixed to the inner surface of the lid 18 near its front away from hinge 22. The pivot 34 includes a spring (not shown) for biasing the handle 28 so that the grip 30 is normally pressed upward against the lid 18.

The lever arm 32 extends past the pivot 34 and is there attached to a stopper 36 so that when the grip 30 is pulled downward away from the lid 18, as would be the case where the handle 28 being used to pull the lid 18 to a closed position, the stopper 36 is pressed close to the lid 18 to cover an orifice 38 cut in the lid 18. Together the stopper 36 and orifice 38 make up a pressure valve 40.

The length of the lever arm 32 between the pivot 34 and the grip 30 is substantially longer than that between the pivot 34 and the stopper 36 so that with modest pressure by the individual 16 downward on the grip 30, substantial pressure is exerted by the stopper 36 against the orifice 38 preventing the flow of air through the orifice 38. The orifice 38 has a cross-sectional area of approximately one square inch. Accordingly, for reduction in pressure within the chamber 10 of approximately 0.35 psi to 0.7 psi, far less than a pound of force is required to hold the stopper 36 against the orifice 38. This force is further reduced by the mechanical advantage of the lever 32.

During operation of the chamber 10, the individual 16 grabs the grip 30 pulling it downward to close the lid 18 onto the base 12. At the same time, the stopper 36 is pressed against the orifice 38 preventing the flow of air therethrough. Next, air is removed from the chamber by means of pump unit 42. As pressure in the chamber is reduced, the lid 18 is pressed against the base 12 by the weight of outside air pressure compressing the gasket 24 as has been described. Even small reductions of pressure produce considerable force over the large area of the lid 18 to deform the gasket 24 without the need of additional locking levers and the like. As will be described, the elimination of clamps or other mechanical levers makes exiting the chamber less difficult and faster.

As pressure is reduced the pressure and volume are measured and used to calculate a final static pressure. The pump 42 is then reversed, returning air to the chamber 10. At any time prior to the conclusion of the test, the grip 30 may be released causing the grip 30 to move upward toward the lid 18 releasing the stopper 36 from the orifice 38 under the influence of the spring within the pivot 34. Air may therefore flow in through the orifice 38 releasing the pressure against the lid 18 permitting it to be opened. This ability to open the lid 18 will be available despite operation of the pump used to reduce the pressure within the chamber 10 as will be described.

Pump unit 42 is designed to provide accurate volume measurements of the air removed and incorporates two cylindrical vessels 44 and 46 closed at the top and suspended by cables 48 and 50 respectively from a cylindrical shaft 52. The cables 48 and 50 are wound in counterclockwise and clockwise directions around the shaft 52 respectively so that with rotation of the shaft 52 in a clockwise direction, vessel 44 rises and vessel 46 falls by equal amounts. Conversely, counterclockwise rotation of the shaft 52 causes vessel 44 to fall and vessel 46 to rise. The cables 48 and 50 are wound on a shaft in a nonoverlapping condition so that a given rotation of the shaft 52 produces a constant vertical motion of the vessels 44 and 46. Vessels 44 and 46 are stabilized by tracks 54 positioned on either side of the vessels 44 and 46 so as to eliminate lateral or torsional motion of these vessels. It will be recognized that a rack and pinion gear or other well known displacement mechanisms may be used instead of cables.

Shaft 52 is connected to a stepper motor 56 controlled by stepper motor circuitry 58. The stepper motor circuitry 58 also connects with the microprocessor I/O card 23 so that the computer 25 may control rotation of the shaft 52 as will be described. For a typical stepper motor, 200 steps provide 360° of revolution thus by controlling the number of steps, the offset of the vessels may be accurately determined.

Each of vessels 44 and 46 contain sufficient water so as to be halfway full when both vessels 44 and 46 are at the vertical height (i.e. have zero offset). A flexible hose 59 interconnects the volumes of each of the vessels 44 and 46 through their bottom walls so as to permit the passage of the water between vessels 44 and 46. Vessel 44 also has a flexible hose 60 attached to an orifice at its upper end so as to permit the flow of air between the vessel 44 and the chamber 10 through the hose 60. An orifice in the upper end of vessel 46 communicates directly with the atmosphere.

Although generally the weight of vessels 44 and 46 is counterbalanced on shaft 52 as a result of the counterwound cables 50 and 48, however, this counterbalance can only account for the constant weights of the vessels 44 and 46, not for any contained liquid moving therebetween. Accordingly, the stepper motor 56 is sized to turn the shaft 52 against an offset weight of liquid contained within the vessels 44 and 46. Additionally, an extension spring (not shown) attached to the vessels 44 and 46 may be used to offset their increasing weight as water flows into them as they are lowered.

Generally then, when the shaft 52 is rotated in the clockwise direction, vessel 44 will rise and water will move through hose 59 to vessel 46. This drop in the level of the water in vessel 44 will draw additional air from the chamber 10 through the hose 60 thus reducing the pressure in the chamber 10. Unlike a standard air pump the action of the pump unit 42 is to remove air from the chamber 10 in a controlled and measurable way. In particular, the pump unit 41 serves to controllably increase the effective volume of the chamber 10 when closed thus providing a continuously controlled decompression. For this reason pump unit 42 will be termed a "volumetric" pump which will henceforth refer to any pump which permits accurate, instantaneous measure of the effective increase in volume provided by the pump.

The chamber volume is approximately 380 liters in a preferred embodiment and thus 25 cm. pressure head requires a change of volume of 410 ml. The vessels 44 and 46 are therefore sized to be somewhat more than twice this volume.

Referring now to FIGS. 1 and 2, the instantaneous displacement volume of the pump unit 42, representing the increment in volume that the pump 42 adds to or subtracts from the volume of the chamber 10, may be determined by a combination of the measuring of the offset L of the two vessels 44 and 46 calculated from rotation of the shaft 52 and the measuring of the air pressure within the vessel 44 by pressure transducer 29 attached to the chamber 10 and communicating with the vessel 44 via hose 60.

Absent any difference in air pressure between the volumes of vessel 44 and 46, a vertical displacement of those vessels with respect to each other of L would be expected to cause a change in the water level in those vessels of L as the water flowed through hose 59 between the vessels 44 and 46 to seek its own level. In practice however, because the change in the height of the water in vessel 44 causes a corresponding change in the air pressure within vessel 44 (dependent in part on the volume of chamber 10), a full change in the height of the water within vessel 44 equal to L cannot be expected. Instead, in the case where vessel 46 is dropped by a distance L with respect to vessel 44, as the water level in vessel 44 drops with the flow of water between vessels 44 and 46, the air pressure within vessel 44 drops providing a pressure difference which counteracts to some extent the gravitational flow through hose 59. When a static condition is reached, the water will have dropped by an amount less than L as a result of this decreased pressure. The height of the water will in fact remain at a level P above L where P is the pressure difference between the air in vessels 44 and 46 expressed in a column height of the particular liquid. For example, if there is a pressure difference between the air in vessels 44 and 46 of 0.3 psi, P will equal approximately 25 cm. Thus, the total drop in water height within vessel 44 will equal L minus P.

This drop in height of the water may be readily converted to a change in volume of chamber 10 by fashioning vessel 44 as a cylinder and making use of the volumetric formula for a cylinder. Specifically, the change in volume will equal $(L-P)\pi(D/2)^2$ where D is the diameter of the cylindrical vessel 44.

Generally, the operation of the chamber 10 for computation of density comprises the following steps. The individual 16 enters the chamber resting on the platform 19. After a weight figure is obtained by means of load cells 21 communicating with computer 25, the individual is instructed by means of a message on the display of the computer 25 or an operator to grasp the handle 28 pulling the lid 18 down to the base 12 in a closed position. This grasping of the handle, as has been described, closes the pressure valve 40 and activates the proximity switch 31 providing a signal to the computer 25 that depressurization may occur. The computer 25 then provides signals to the stepper motor circuitry 58 causing the stepper motor to turn the shaft 52 raising vessel and lowering vessel 46 to create an offset value L as has been described to produce a desired reduction in pressure in the chamber 10. This reduction in pressure serves further to seal the chamber 10 compressing the gasket 24. During the operation of the pump 42, pressure and temperature values are read from the transducers 29 and 27.

Once sufficient data is collected, commands are provided to the stepper motor to return the vessels 44 and 46 to equal height thus restoring pressure to the chamber 10 and instructions are provided to the individual 16 to release the handle 28 and to exit the chamber 10.

The volume of the individual 16 may be computed by employing static pressure measurements before and after reduction in pressure of the chamber together with the known chamber volume and the known change in volume of the chamber caused by the pump unit 42 in the following equation reflecting Boyle's law.

$$\frac{P_1 V_1}{T_1} = \frac{P_2(V_1 + \Delta V)}{T_2} \tag{1}$$

where:

$P_1$ and $P_2$ are the absolute pressures before and after operation of the pump unit 42;

$V_1$ is the volume of the chamber 10 minus the volume of the patient;

$\Delta V$ is the change in volume affected by the pump unit; and $T_1$ and $T_2$ are the absolute temperatures before and after reduction in pressure by the pump unit 42. This equation may be solved for the volume of the patient $V_P$ based on the known chamber volume $V_0$ as follows:

$$V_P = V_0 - V_1 \tag{2}$$

The pumping down of the chamber 10 may cause some reduction in the chamber volume and accordingly a correction factor may be produced by first measuring the chamber without an individual 16 in it. In this case, equation 1 becomes:

$$\frac{P_1 V_1}{T_1} = \frac{P_2[V_1 + \Delta V - V_E]}{T_2} \tag{3}$$

where:

$V_E$ is the change in the volume of the chamber 10 caused by the pressure reduction and is assumed to be a function of pressure. $V_E$ may be determined by conducting at least two depressurizations to the same pressure reduction with the chamber occupied by different bodies of known volumes so that $V_1$ may be eliminated algebraically. Assuming then that $\Delta V$ is known for both depressurizations, then the value $V_E$ may be determined and used to correct for values of $V_1$ in later measurements.

In the preferred embodiment, the ability of the pump unit 42 to provide a continuous stream of volume data as the pumping occurs is used to improve the accuracy of the measurement and the speed of the measurement process. Referring now to FIGS. 1, 2 and 5(a), under the control of the computer 25, the command issued to stepper motor 56 to provide an offset between vessels 44 and 46 of L', where L' is the anticipated offset needed to produce the desired pressure drop in the chamber 10. The hose 59 communicating between the vessels 44 and 46 is sized such that at the desired rate of depressurization, i.e., the flow of water from vessel 44 to vessel 46, can keep up with the change in height of those vessels caused by the rotation of shaft 52. Accordingly, the offset L of the vessels 44 and 46 indicated by line 72 of FIG. 5(a) closely tracks the actual water level 74 and hence the change in volume provided by the pump unit 42.

As the offset L increases with motion of the shaft 52, sample points are taken of the pressure from pressure transducer 29 to derive pressure-volume data pairs 78. These volume and pressure data pairs are shown in FIG. 5(b) in which pressure is plotted against the inverse of volume. The data pairs 78 generally follow a straight line 79. As additional points are collected, the accuracy with which the line 79 can be determined increases until the intersection of this line 79 with the desired volume level L may be computed to provide an indicated pressure P', even prior to the offset between vessels 44 and 46 reaching the indicated offset L'.

Once the desired offset L' is reached, momentum of the water through hose 59 causes an overshoot 82 producing points 78' not on line 79. As the oscillating water level indicated by line 74 approaches the desired offset L', these points 78' spiral inward to converge at point P'. This decaying oscillation of the water level may take some time and yet by using the data provided on a continuous basis from the pump unit 42, the volume of the individual 16 may be computed even prior to the water level so stabilizing. The use of these multiple sample points during the acquisition of data also allows periodic phenomenon such as respiratory motion to be discounted in the ultimately determined pressure value P'.

Most simply points 78 prior to reaching L' are fitted by linear regression or other known fitting techniques to a line 79 used to calculate the final value P' as described.

Alternatively, values 78' after the offset L' has been reached, may be simply averaged if time allows to produce true static value. This latter technique is preferred for use in determining the volume of the chamber without the individual 16 as has previously been described.

The above description has been that of a preferred embodiment of the present invention. It will occur to those that practice the art that many modifications may be made without departing from the spirit and scope of the invention. For example, the sampled pressure and volume data may be used to calculate the effect of the momentum of the water on the volume as the rate of depressurization is increased so as to provide even more rapid operation. In order to apprise the public of the various embodiments that may fall within the scope of the invention, the following claims are made.

I claim:

1. An apparatus for measuring the volume of a breathing subject comprising:
    a substantially air-tight chamber having a chamber volume sized to receive the subject;
    a pump communicating with the volume to monotonically change the air-pressure within the chamber volume during a test period;
    a pressure gauge communicating with the chamber volume to produce a pressure signal indicating the pressure within the chamber volume;
    a sampling means for sampling the pressure signal at a plurality of times during the test period to produce sampled pressure values;
    calculating means for predicting a static pressure from the sampled pressure values and calculating a volume of the subject from the static pressure;
    display means for display an indicating of the volume of the subject; and
    wherein calculating means performs a linear regression of the sampled pressure values from the beginning of the test period to calculate the static volume of the subject.

2. The apparatus of claim 1 wherein the sampling means samples the pressure signal to obtain pressure values at different chamber volumes.

3. An apparatus for measuring the volume of a breathing subject comprising:
    a chamber having an aperture with a first lip through which the subject may be received into a volume;
    a lid having a second lip sized to abut the first lip when the lid is in a closed position;
    a pump communicating with the volume to decrease the air-pressure within the volume so as to draw the lid and chamber together to form an air-tight enclosure;
    a pressure gauge communicating with the volume to produce a pressure signal indicating the pressure within the volume;
    calculation means for calculating the volume of the subject from the pressure signal; and
    display means for displaying an indication of the volume of the subject;
    wherein the lid is hinged to the chamber and including further a spring for biasing the lid away from the chamber to an open position and a handle positioned so as to be grasped by the subject so that the subject may move the lid to the closed position against the biasing of the spring from within the chamber;
    including further a pressure relief valve having a movable stem and operating to permit the passage of air through an orifice into the volume, the pressure relief valve stem being attached to the handle so as to permit the passage of air into the volume when the handle is not grasped by the subject and so as not to permit the passage of air into the volume when the handle is grasped by the subject to hold the lid closed.

4. The apparatus of claim 3 wherein the first and second lip are each substantially planar.

5. The apparatus of claim 3 wherein one of the first and second lips includes an elastomeric gasket positioned to be compressed between the first and second lips.

6. An apparatus for measuring the volume of a breathing subject comprising:
    a substantially air-tight chamber having a volume sized to receive the subject;
    a pressure gauge communicating with the volume to produce a pressure signal indicating the pressure within the volume;
    a pump communicating with the volume to change the air-pressure within the chamber volume during a test period, the pump comprising;
    a first container having a first and second opening, the second opening communicating with the chamber volume;
    a second container having a first opening communicating with the first opening of the first container, the second container movable vertically with respect to the first container;

a liquid for being placed in the first and second containers to flow therebetween with changes in the relative vertical placement of the two containers moving air between the chamber volume and the first container when the liquid flows between the first container and the second container in response to relative vertical movement of the first container; and calculation means for calculating the volume of the subject from the pressure signal and the volume displaced by the pump.

7. The apparatus of claim 6 wherein the first container is of uniform horizontal cross-section so that its vertical displacement is directly proportional to the volume of liquid flow between the first and second containers.

8. The apparatus of claim 6 wherein the pressure gauge produces an electric signal and the second container is movable with respect to the first container by an electric actuator and wherein the calculation means is an electronic computer communicating with the pressure gauge and the electric actuator and operating according to a stored program to:

a) cause the electric actuator to move the first container in a first vertical direction until a predetermined pressure is reached as indicated by the pressure gauge;

b) subtract the pressure expressed in the height of a supported column of the liquid from the moved vertical direction to establish an effective displacement height;

c) establish the volume displaced by the pump based on the effective displacement height times the cross sectional area of the first.

* * * * *